US009642645B2

(12) United States Patent
Smith et al.

(10) Patent No.: US 9,642,645 B2
(45) Date of Patent: May 9, 2017

(54) TISSUE CUTTING DEVICES AND METHODS (71) Applicant: Boston Scientific Scimed, Inc., Maple Grove, MN (US)

(72) Inventors: Paul Smith, Smithfield, RI (US); Samuel Raybin, Marlborough, MA (US); Naroun Suon, Lawrence, MA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 348 days.

(21) Appl. No.: 14/205,825

(22) Filed: Mar. 12, 2014

(65) Prior Publication Data

US 2014/0277021 A1    Sep. 18, 2014

Related U.S. Application Data (60) Provisional application No. 61/799,047, filed on Mar. 15, 2013, provisional application No. 61/779,939, filed on Mar. 13, 2013.

(51) Int. Cl.
| | |
|---|---|
| *A61B 17/32* | (2006.01) |
| *A61B 17/3205* | (2006.01) |
| *A61B 17/00* | (2006.01) |
| A61B 17/30 | (2006.01) |

(Continued)

(52) U.S. Cl.
CPC .... *A61B 17/3205* (2013.01); *A61B 17/00234* (2013.01); *A61B 17/320016* (2013.01); *A61B 18/1492* (2013.01); *A61B 2017/00269* (2013.01); *A61B 2017/306* (2013.01); *A61B 2017/320012* (2013.01);

(Continued)

(58) Field of Classification Search
CPC ........ A61B 17/3205; A61B 17/320016; A61B 17/00234; A61B 18/1492; A61B 2018/00202; A61B 2218/007; A61B 2017/320044; A61B 2018/1425; A61B 2017/320012; A61B 2017/00269; A61B 2017/306
See application file for complete search history.

(56) References Cited

U.S. PATENT DOCUMENTS

| | | | |
|---|---|---|---|
| 4,162,678 A | 7/1979 | Fedotov et al. | |
| 5,437,630 A * | 8/1995 | Daniel ............. | A61B 17/32002 604/22 |

(Continued)

*Primary Examiner* — Richard Louis
(74) *Attorney, Agent, or Firm* — Bookoff McAndrews, PLLC (57) ABSTRACT

A medical device may include an elongate member including a proximal end and a distal end. The medical device may also include a rotatable member at the distal end of the elongate member. The rotatable member may be rotatably coupled to the distal end of the elongate member. The rotatable member may include a longitudinal axis, and may be configured to rotate about the longitudinal axis. The rotatable member may also include a gripping element configured to engage a layer of tissue. The gripping element may be configured to selectively couple at least a portion of the layer of tissue to a surface of the rotatable member, to restrict relative movement between the portion of the layer of tissue and the surface of the rotatable member, during rotation of the rotatable member.

10 Claims, 6 Drawing Sheets

(51) Int. Cl.
 *A61B 18/14* (2006.01)
 *A61B 18/00* (2006.01)

(52) U.S. Cl.
 CPC ............ *A61B 2017/320044* (2013.01); *A61B 2018/00202* (2013.01); *A61B 2018/1425* (2013.01); *A61B 2218/007* (2013.01)

(56) References Cited

U.S. PATENT DOCUMENTS

| | | | |
|---|---|---|---|
| 6,183,432 B1 * | 2/2001 | Milo | A61B 17/22012 |
| | | | 604/22 |
| 6,371,906 B1 * | 4/2002 | Borst | A61B 17/02 |
| | | | 128/857 |
| 2002/0082621 A1 | 6/2002 | Schurr et al. | |
| 2003/0083656 A1 | 5/2003 | Morrison et al. | |
| 2003/0163129 A1 * | 8/2003 | Lee | A61B 8/0825 |
| | | | 606/47 |
| 2005/0177184 A1 | 8/2005 | Easley | |
| 2008/0249526 A1 | 10/2008 | Knowlton | |
| 2010/0256662 A1 | 10/2010 | Racenet et al. | |
| 2011/0313247 A1 | 12/2011 | Cox | |
| 2012/0101594 A1 * | 4/2012 | Fogel | A61F 5/0086 |
| | | | 623/23.64 |
| 2012/0143234 A1 * | 6/2012 | Wilson | A61B 19/24 |
| | | | 606/170 |

\* cited by examiner

TISSUE CUTTING DEVICES AND METHODS

CROSS-REFERENCE TO RELATED APPLICATIONS

This application claims the benefit of priority from U.S. Provisional Application No. 61/779,939, filed on Mar. 13, 2013, and U.S. Provisional Application No. 61/799,047, filed on Mar. 15, 2013, each of which is incorporated by reference herein in its entirety.

DESCRIPTION OF THE DISCLOSURE

Field of the Disclosure

Embodiments of the present disclosure generally relate to medical devices and procedures. In particular, embodiments of the present disclosure relate to medical devices for cutting tissue from a portion of a patient's body, and procedures performed with the medical devices.

Background of the Disclosure

Medical devices, such as endoscopes or other suitable introduction sheaths, may be employed for a variety of diagnostic and surgical procedures. Many of these procedures involve cutting and/or removing tissue, such as a layer of tissue, from a portion of a patient's body. In particular, such procedures may be carried out by inserting an introduction sheath into a patient's body through a surgical incision, or via natural anatomical orifices, and performing the procedure or operation with one or more end effectors inserted through the introduction sheath.

Sometimes, procedures may be performed to remove a tissue layer overlaying or adjacent to another tissue layer. On occasion, tissue cutting may be carried out using an electrocautery probe or tool. The probe or tool may be steered to a target site within the patient's body, and a cauterization voltage may be applied to an electrode that forms part of the probe or tool.

However, sometimes, use of conventional cutting probes or tools may result in inadvertent and undesired damaging of an underlying tissue layer at the target site by, for example, cutting or puncturing the underlying tissue layer. In some instances, inadvertent and undesired removal of the underlying tissue layer may occur. This may happen because conventional applied tools may be incapable of adequately controlling depth of penetration into the target site during operations, and further, may be incapable of distinguishing between different types of tissue or layers of tissue. This may cause unnecessary loss of blood and healthy tissues from a patient's body. Moreover, excessive bleeding may add to the difficulty of controlling the cutting tools appropriately.

Therefore, there remains a need for devices and methods that can be effectively used for cutting, resecting, and/or dissecting tissue layers, and may further help avoid undesired and inadvertent damaging or removal of underlying tissue layers during certain medical operations and procedures.

SUMMARY OF THE DISCLOSURE

The present disclosure provides medical devices and methods for cutting, resecting, and/or dissecting one or more layers of tissue from a portion of a human body, and especially during medical procedures.

According to an aspect of the present disclosure, a medical device may include an elongate member including a proximal end and a distal end. The medical device may also include a rotatable member at the distal end of the elongate member. The rotatable member may be rotatably coupled to the distal end of the elongate member. The rotatable member may include a longitudinal axis, and may be configured to rotate about the longitudinal axis. The rotatable member may also include a gripping element configured to engage a layer of tissue. The gripping element may be configured to selectively couple at least a portion of the layer of tissue to a surface of the rotatable member, to restrict relative movement between the portion of the layer of tissue and the surface of the rotatable member, during rotation of the rotatable member.

According to another aspect of the present disclosure, a medical device may include an elongate member including a proximal end, a distal end, a longitudinal axis, and a suction lumen extending from the proximal end to the distal end. The medical device may also include a handle at the proximal end of the elongate member. The medical device may also include a rotatable gripping member at the distal end of the elongate member. The rotatable gripping member may be cylindrical, and rotatably coupled to the distal end of the elongate member. The rotatable gripping member may include a longitudinal axis substantially parallel to the longitudinal axis of the elongate member, and may configured to rotate about the longitudinal axis of the rotatable gripping member. The rotatable gripping member may include a slot having a closed distal end and one or more apertures in fluid communication with the suction lumen. The rotatable gripping member may be configured to engage a portion of a layer of tissue using suction, and hold the portion of the layer of tissue using suction, to restrict relative movement between the portion of the layer to tissue and a surface of the rotatable gripping member during rotation of the rotatable member, and pull the layer of tissue away from an underlying layer of tissue. The handle may be configured to control operation of the rotatable gripping member. The medical device may also include a cutting device at the distal end of the elongate member, configured to cut the layer of tissue.

According to another aspect of the present disclosure, a method for performing a medical procedure on a layer of tissue may include engaging the layer of tissue with a gripping element of a rotatable member rotatably coupled to a distal end of an elongate member. The method may also include gripping at least a portion of the layer of tissue with the gripping element to selectively couple the portion of the layer of tissue with a surface of the rotatable member, to restrict relative movement between the portion of the layer to tissue and the surface of the rotatable member. The method may also include rotating the rotatable member about a longitudinal axis of the rotatable member to move the layer of tissue. The method may also include cutting the layer of tissue.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out below.

It is to be understood that both the foregoing general description and the following detailed description are exemplary and explanatory only and are not restrictive of the disclosure.

BRIEF DESCRIPTION OF THE DRAWINGS

The accompanying drawings, which are incorporated in, and constitute a part of this specification, illustrate exemplary embodiments of the present disclosure and, together with the description, serve to explain the principles of the disclosure.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts. Also, any aspect set forth in any embodiment may be used with any other embodiment set forth herein.

Overview

Embodiments of the present disclosure relate to devices and methods used in medical procedures like tissue cutting, Endoscopic Mucosal Resection ("EMR"), Endoscopic Mucosal Dissection ("EMD"), and Endoscopic Submucosal Dissection ("ESD"). Such devices may cut, resect, and/or dissect one or more tissue layers at a target site of a patient's body, while leaving one or more underlying tissue layers intact. One exemplary medical device may include an elongate member having one or more lumens, tubular members, and/or torsional elements, extending therethrough. Connections to a handle, suction device, and/or torsion device may be located at or near a proximal end of the elongate member, and a suitable end-effector may be located at or near a distal end of the elongate member. The end-effector may include a rotatable member, which may be precisely controlled and manipulated by an operator or surgeon from the proximal end of the elongate member. Components of medical devices of the present disclosure, and steps of methods of the present disclosure, will be explained in further details hereinafter, in conjunction with the accompanying figures.

The terms "proximal" and "distal" are used herein to refer to the relative positions of the components of the exemplary medical devices. When used herein, proximal" refers to a position relatively closer to the surgeon using the medical devices. In contrast, "distal" refers to a position relatively further away from the surgeon using the medical devices, or closer to a surgical site located within the patient's body.

Exemplary Embodiments

Figure 1A:
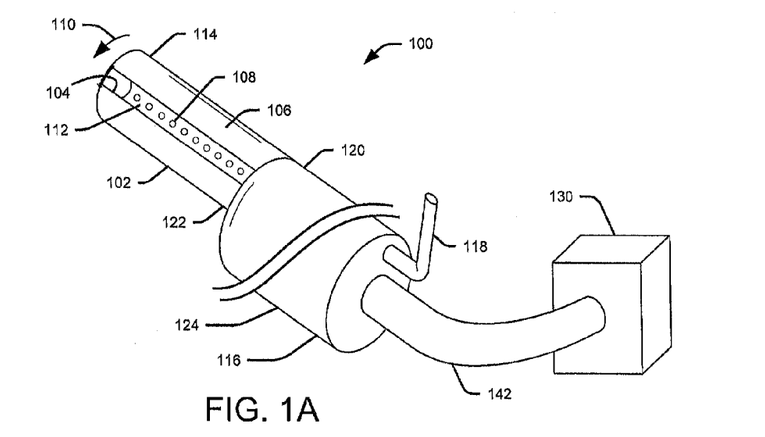
FIG. 1A illustrates an exemplary medical device employing a rotatable member, according to an embodiment of the present disclosure.

FIG. 1A illustrates an exemplary medical device 100 according to an embodiment of the present disclosure. The device 100 may include a rotatable member 102 having an outer or lateral surface 106 and a closed distal end. Though shown as being substantially cylindrical, the rotatable member 102 may also have any other shape suitable for gathering tissue in a rolling motion, including, for example, a shape with an elliptical, ovular, polygonal, or irregular cross-section.

The rotatable member 102 may include a channel or slot 104. One or more openings 108 may be provided on one or more surfaces of the slot 104, including a surface 112 of the slot 104. Each of the openings 108 is shown as being circular in shape, however, it should be understood that the openings 108 may be of any suitable shape including, for example, elliptical, ovular, rectangular, or irregular shapes. It should also be understood that the slot 104 may have any suitable shape, including, for example, one with a substantially flat bottom surface 112.

When the medical device 100 is used, the rotatable member 102 may be inserted through an elongate member 124 to a distal end 120 of the elongate member 124, or otherwise positioned at the distal end 120. The elongate member 124 may include a sheath, catheter, endoscope, and/or any other suitable tubular structure, configured to be inserted within a patient's body. For example, the rotatable member 102 may be coupled to an elongate member (not shown), and the rotatable member 102 and the elongate member may be sized and configured to slide distally and proximally through a lumen within the elongate member 124. The rotatable member 102, or the rotatable member 102 and at least a portion of the elongate member, may be extended out a distal opening (not shown) of the elongate member 124 to perform a procedure, and may be retracted into the distal opening during insertion and/or removal of the elongate member 124 from a target site in a patient's body.

Positioning of the rotatable member 102 at the distal end 120 of the elongate member 124 may take place before the elongate member 124 is navigated to a target site in a patient's body, or after the elongate member 124 is navigated to the target site, with the distal end 120 at the target site. The rotatable member 102 may engage a layer of tissue at the target site. The rotatable member 102 may be made of one or more widely available biocompatible materials, and/or may be coated with an appropriate material to ensure its unreactive and safe engagement with the layer of tissue and other parts of the patient's body.

The medical device 100 may be sized and formed to pass through body lumens, and/or lumens in other medical devices, so the medical device 100 can be introduced into the body of a patient. The exact dimensions and the overall structure of the rotatable member 102 may vary in different embodiments, and may also depend upon characteristics of the target site of the patient's body being treated.

At a distal end 114, the rotatable member 102 may form a distal end portion of the medical device 100. At a proximal end 122, the rotatable member 102 may be rotatably coupled to the elongate member 124. Additionally or alternatively, the rotatable member 102 may be rotatable coupled to an elongate member (not shown) that extends through a lumen in the elongate member 124. The elongate member may include, for example, a substantially cylindrical shaft. It is also contemplated that the rotatable member 102 may be detachably coupled to the elongate member 124, to facilitate its removal and/or replacement, when desired.

At its proximal end 116, the elongate member 124 may include provisions, devices, and/or device interfaces that may enable a user to manipulate or control movement of the rotatable member 102, and/or a distal end 120 of the elongate member 124. For example, a handle 118 may be disposed at the proximal end 116, as shown schematically in FIGS. 1A and 1B, for steering or otherwise actuating the rotatable member 102. More specifically, to operate the rotatable member 102, one or more actuating members (discussed below) may extend through the elongate member 124. The actuating members may include, for example, one or more control wires, rods, braided cables, shafts, and/or torsional elements, connecting the handle 118 to the rotatable member 102. When the handle 118 is operated, the actuating members may push, pull, and/or rotate the rotatable member 102 to facilitate a desired operation. It is contemplated that the one or more actuating members may pass through one lumen in the elongate member 124, or through multiple lumens, wherein each lumen may have one or more actuating members, to facilitate control and operation of the rotatable member 102 using the handle 118.

Figure 1B:
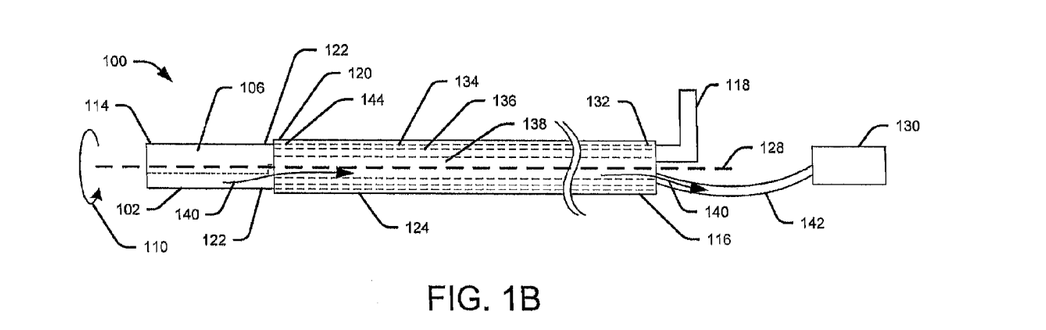
FIG. 1B is a side view of the exemplary medical device of FIG. 1A, with certain interior components illustrated, according to an embodiment of the present disclosure.

At the proximal end 116, the elongate member 124 may be connected to a conduit 142, which may be further connected to a vacuum source 130, as shown in FIGS. 1A and 1B. Specifically, the conduit 142 may connect one or more lumens 138 extending through the elongate member 124 to the vacuum source 130. During operations or use, such a connection may facilitate maintenance of a low pressure region within the one or more lumens 138. At their distal ends, the one or more lumens 138 extending within the elongate member 124 may communicate with one or more openings 108. This creates suction force at and/or within the slot 104, allowing the slot 104 to act as a gripping element. This suction force may assist in extracting a layer of tissue from the target site where the rotatable member 102 is positioned. The vacuum source 130 may be configured to maintain an appropriate amount of pressure within the one or more lumens 138 extending within the elongate member 124, and the maintained pressure may be sufficient to extract one or more desired layers of tissue at the target site, without extracting the underlying layers. However, the pressure existing within the one or more lumens 138 of the elongate member 124 may be controllable or adjustable by controlling or adjusting the vacuum source 130. Any suitable vacuum source known in the art, and having the appropriate desired capacity for extracting tissue layers, may be used.

FIG. 1B depicts a side view of the medical device 100, and shows certain interior components. As depicted, an actuation member 134 may be positioned longitudinally within the elongate member 124. The actuation member 134 may be positioned substantially parallel to a longitudinal axis 128 of the elongate member 124, or positioned so as to be centered around the longitudinal axis 128. The actuation member 134 may act as a torsional element, configured to transfer torque from the proximal end 116 to the distal end 120 of the elongate member 124, and to the rotatable member 102, to facilitate rotation of the rotatable member 102.

The handle 118 may be used to generate the torque whenever actuation of the rotatable member 102 is desired. For example, a proximal end 132 of the actuation member 134 may be connected to the handle 118, and a distal end 144 of the actuation member 134 may be connected to the rotatable member 102, to transfer torque applied by an operator at the handle 118 to the rotatable member 102. The actuation member 134 may include, for example, a flexible shaft composed of a suitable high grade material that may support effective torque transfer. Further, the amount of torque transferred may be easily controllable by manipulating the handle 118. It is contemplated that the handle 118 may include a manually driven torque input device including, for example, a rotatable knob (not shown).

It is also contemplated that the actuation member 134 may be connected to a powered torque input device that may be electrically, pneumatically, and/or or hydraulically driven, to provide torque. Such an input device may be directly connected to the actuation member 134, or connected to the actuation member 134 by the handle 118, with controls provided at the handle 118 for operating the device.

At the distal end 144, the actuation member 134 may be connected to the rotatable member 102, so that rotation of the distal end 144 produces rotation of the rotatable member 102. The structure of the actuation member 134 may be such that rotation initiated at its proximal portion 132 may be quickly and efficiently transferred along its length, towards its distal portion 144. The distal end 144 may therefore rotate quickly in response to a rotation initiated at the proximal end 132.

A tubular member 136 may extend at least partially through the actuation member 134, as shown in FIG. 1B. The tubular member 134 may extend substantially along the longitudinal axis 128 of the elongate member 124. The tubular member 136 may be a suction tube, and may have a lumen 138. A low pressure region may be created within the lumen 138 by the vacuum source 130, connected thereto by the conduit 142. Although one lumen is shown herein, multiple lumens of the type 138 may be provided to extend through the actuation member 134, in embodiments. The lumen 138 may be in fluid communication with the openings 108, to facilitate suction through the openings 108, and enable extraction of a layer of tissue toward and into the slot 104 in the rotatable member 102. It is contemplated that in one embodiment, a channel may be provided connecting the lumen 138 to the openings 108, to facilitate flow of the air sucked through the openings 108, into the lumen 138, and eventually, into the vacuum source 130. In a case where multiple lumens extend through the actuation member 134, multiple channels may be provided to connect the openings 108 to the lumen 138, individually.

Optionally, the tubular member 136 and the actuation member 134 may be integrated and formed as a single unit, to enable ease in manufacture, assembly, and operation. For example, a single tubular member, may be positioned coaxial with and within the elongate member 124, to act as the actuation member. An interior portion of that member may communicate with the vacuum source 130. That interior portion may then act as a suction tube, maintaining a region of low pressure therein. The single tubular member may be a braid-reinforced tube capable of acting as the torsional or rotation transmitting element and the suction tube.

As an operator activates the medical device 100, the vacuum source 130 may initiate suction of air from the target site, at a specific flow rate, by creating a low pressure region within the lumen 138. The direction shown by the arrows 140 illustrates the path of flow for the suctioning from the slot 104 and through the lumen 138, once the vacuum source 130 starts operating. When a minimum pressure threshold is attained within the lumen 138, which may be provided through an audible, digital and/or and analog interface, well known to the skilled in the art, the operator may reach out to a layer of tissue targeted for cutting, resection, and/or dissection. Accordingly, as soon as the rotatable member 102 is positioned on, adjacent, or otherwise close enough to that layer of tissue, the suction force at the slot 104 and the openings 108 may lift or pull a portion of the tissue layer onto and/or into the slot 104. This provides an initial state of tissue acquisition or gripping. The rotatable member 102 may then be rotated through the actuation member 134 and/or handle 118, or through an alternative torque transfer mechanism, to wrap the pulled or lifted layer of tissue around the outside surface 106 of the rotatable member 102.

Figure 2A:
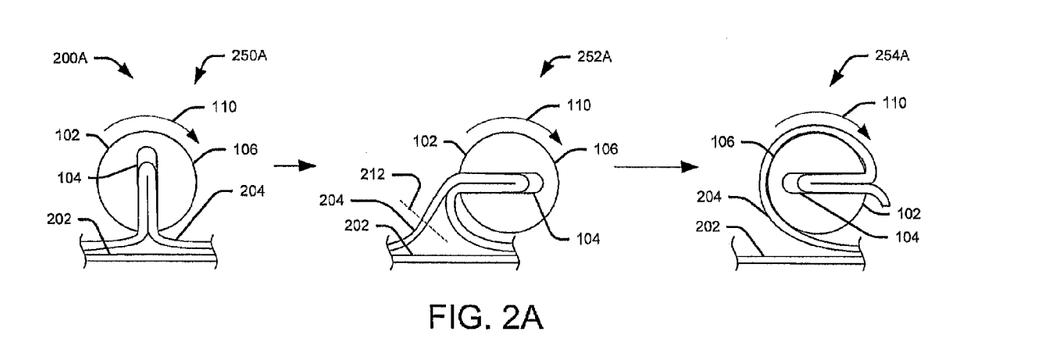
FIG. 2A shows partial end views of the rotatable member of the medical device of FIG. 1A in three operative stages, in accordance with an embodiment of the present disclosure.

A sequential series of steps 200A, including the initial extraction and pulling of the targeted layer of tissue, and its wrapping over the lateral surface 106 of the rotatable member 102, and its cutting, is illustrated in FIGS. 2A-2D. Specifically, FIG. 2A depicts a partial front view of the rotatable member 102, in three sequential phases of operation at a target site. Among a stack of many tissue layers at the target site, a top tissue layer 204 may be one the user wants to cut, resect, or dissect. A bottom tissue layer 202 may lie directly underneath the layer 204. It should be understood that in some parts of the human body, several tissue layers may be stacked one on top of the other. The top tissue layer 204 may be, for example, a mucosal layer, and the layer 202 may be a submucosal layer. Alternatively, the top tissue layer 204 may be a combination of layers, such as the mucosal layer and the submucosal layer, while the layer 202 may be a muscle layer.

At a first stage 250A of the series 200A, the rotatable member 102, through suction force generated by the vacuum source 130, may grasp and draw at least a portion of the top tissue layer 204 onto and/or into the slot 104. Once grasped, an operator may initiate rotation of the rotatable member 102 via the handle 118, in the direction of the arrow 110. An imaging device (not shown) may be inserted through the elongate member 124 and out its distal end 120, allowing the user to visually determine whether the portion of the tissue layer 204 has been sufficiently grasped.

A second operational stage 252A shows the orientation of the rotatable member 102, rotated by about 90° clockwise. During the transition from the operational stage 250A to the stage 252A, the rotatable member 102 may lift the top tissue layer 204, causing that layer to stretch out and/or separate from the bottom tissue layer 202. Further, at this stage, a cutting extender 210 (shown in FIG. 2D) coupled to or located near the rotatable member 102, may be extended out to cut the top tissue layer 204 at a section 212, using a cutting tool 206 coupled to the cutting extender 210. The imaging device (not shown) may be used to determine when and where to make the cut.

The cutting extender 210 may be positioned substantially parallel to a longitudinal axis of the rotatable member 102. It is contemplated that the cutting extender 210 may extend through a lumen (not shown) in the elongate member 124 to a proximal end 116 of the proximal member 124, and/or to an actuation mechanism (not shown) on the handle 118. The handle 118 may be used to extend and retract the cutting extender 210, and to actuate the cutting tool 206. Examples of the cutting tool 206 may include an electrocautery cutting wire, a hook, a blade, and/or a combination of these, to accomplish the cutting operation. It is also contemplated that the cutting extender 210 and the cutting tool 206 may be positioned within the slot 204, to cut at least a portion of the tissue in the slot 204.

At a third operational stage 254A, the operator has rotated the rotatable member by about 270°, with reference to its initial orientation. When this stage is reached, the cutting tool may be drawn out (or done so again), to cut another portion of the layer 204, to obtain a fully resected piece of tissue.

Once the three operation stages 250A, 252A, and 254A, are complete, other subsequent operations, such as electrocauterization using snares, and the like, may be carried out easily and effectively. Further, the orientations of the rotatable member 102, in the shown three operation stages, are merely exemplary, and pauses in the rotation of the rotatable member 102, to perform cutting, may take place during any other appropriate intermediate orientations or angular positions of the rotatable member 102. Further, certain embodiments may incorporate comparatively more or less frequent cutting operations on the wrapped tissue layer, during the rotation of the rotatable member 102. Also, in certain cases, the drawn tissue layer 204 may first be substantially wrapped around the lateral surface of the rotatable member 102, until or beyond the operational stage 254A, before performing any cutting operation. However, at least one embodiment of the present disclosure includes sequential cutting accompanying the rotation of the rotatable member 102, for smooth resection of the layer 204, keeping the underlying layer 202 intact. In all stages, the imaging device (not shown) may help the user position the layer of tissue and the portions of the medical device 100.

In some embodiments, the cutting extender 210 (see FIG. 2D) may move in relation to the rotatable member 102, along a direction substantially parallel to the longitudinal axis 128. Alternatively, the cutting extender 210 may be positioned over the lateral surface 106 of the rotatable member 102, and may be configured to slide thereon, to facilitate cutting of the top tissue layer 204 after positioning by the rotatable member 102. This will be explained in further details hereinafter, in conjunction with FIG. 3.

Figure 2B:
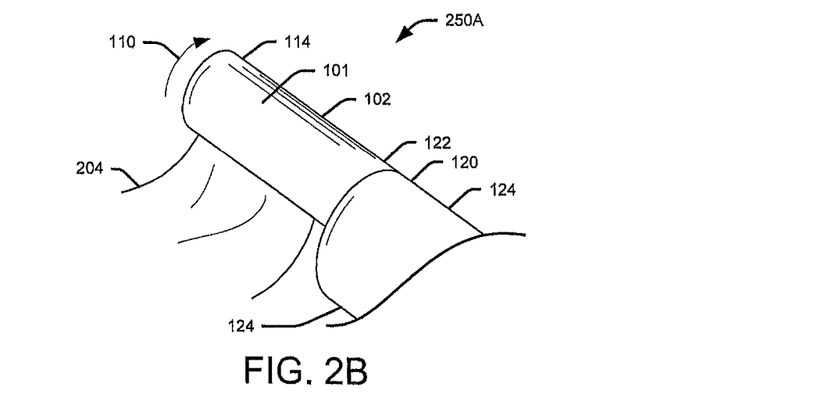
FIG. 2B is a partial perspective view of the medical device of FIG. 1A, shown in one operative stage, in accordance with an embodiment of the present disclosure.
Figure 2C:
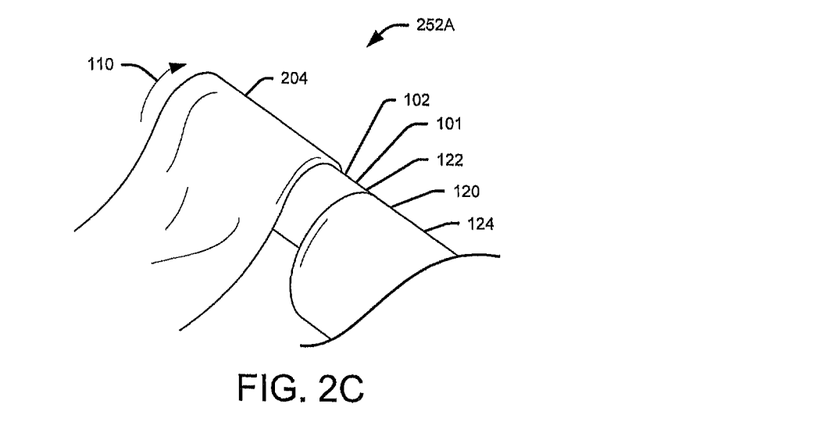
FIG. 2C is another partial perspective view of the medical device of FIG. 1A, shown in another operative stage, in accordance with an embodiment of the present disclosure.

FIG. 2B and FIG. 2C are perspective views of the rotatable member 102 of the medical device 100 of the present disclosure, showing the rotatable member 102 in operational stages 250A and 252A, one following the other. As is apparent from FIG. 2B, the tissue layer 204 is drawn into the slot 104, and is about to wrap tissue around the lateral surface 106 of the rotatable member 102 with its rotation. Following this, FIG. 2C shows the stage when the layer 204 is wrapped around the rotatable member 102 by rotation of the rotatable member 102.

Figure 2D:
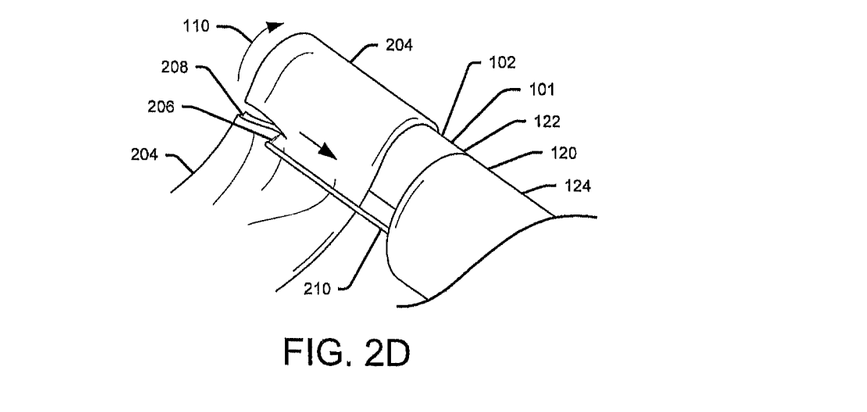
FIG. 2D is another partial perspective view of the medical device of FIG. 1A, shown in another operative stage, in accordance with an embodiment of the present disclosure.

FIG. 2D depicts a part of operational stage 252A, where the cutting extender 210 is shown extended out of the distal end 120 of the elongate member 124, to cut the wrapped portion of the layer 204 using the cutting tool 206. An operator may vary the time and duration of extension of the cutting extender 210, to perform the cutting operation whenever desired. Such a variation may depend on the amount and/or type of tissue that has been targeted. As shown, a cut portion 208 of the wrapped layer 204 may be obtained.

Figure 3:
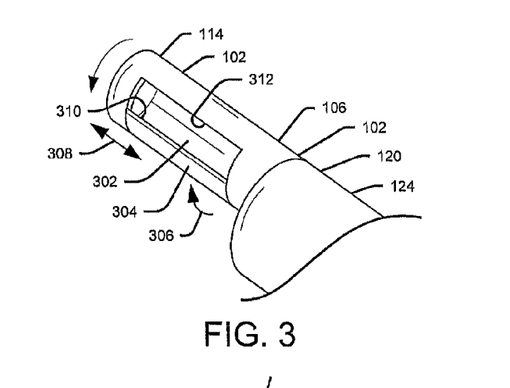
FIG. 3 is a partial perspective view of another exemplary medical device, in accordance with an embodiment of the present disclosure.

Certain embodiments of the present disclosure may utilize different versions of the rotatable member 102. The descriptions below, pertaining to FIGS. 3, 4, 5A, 5B, and 6, explain various alternative embodiments. FIG. 3 depicts an embodiment where the rotatable member 102 may include an opening 302 provided on its outer surface 106. The opening 302 may be configured to receive a gripping element and/or cutting tool, which may be a curved blade 304. The curved blade 304 may be configured to slide at least partially across the opening 302, to engage a layer of tissue. For example, the blade 304 may pinch a portion of tissue between a sharp edge 310 and an edge 312 of the opening 302. To achieve this, the blade 304 may rotate along an interior surface of the rotatable member 102. The blade 304 may sweep across the opening 302 in a lateral direction, with its direction of movement shown by the arrow 306. The sharp edge 310 of the blade 304 may cooperate with the edge 312 of the opening 302 to pinch or clamp a portion of a tissue layer. The rotatable member 102 may then be rotated to lift the tissue layer, and further rotation may wrap the tissue layer about the rotatable member 102 in a manner similar to that described with respect to FIGS. 2A-2D.

To perform a cutting operation on the engaged tissue layer, the blade 304 may be rotated further in the direction of the arrow 306 to force a portion of the tissue layer against the edge 312 of the opening 302, such that the edge 310 of the blade 304 and the edge 312 may shear the portion of the tissue in a scissor-like fashion. Additionally or alternatively, cutting of the tissue may be achieved using a cutting element and cutting tool similar to the cutting extender 210 and cutting tool 206, shown in FIG. 2D. Additionally or alternatively, the blade 304 may be slid longitudinally within the opening 302, substantially parallel to the longitudinal axis of the rotatable member 102, along one or both of the paths represented by arrows 308, to produce a slicing action with the edge 310. It is also contemplated that the blade 304 may be reciprocated by moving the blade 304 along one of the paths represented by the arrows 308, and then moving the blade 304 along the other of the paths in the opposite direction, to facilitate cutting. Appropriate mechanisms may be used to facilitate rotation of the blade 304 along the direction shown by the arrow 306, and/or longitudinal sliding along the arrows 308, within the opening 302. For example, the blade 304 may be coupled on a proximal end to a distal end of a rotatable and/or extendable/retractable shaft or tube (not shown) extending through the elongate member 124. That shaft or tube may extend, for example, through the lumen 138 of the elongate member 124, or around the actuation member 134 and/or the tubular member 136. A proximal end of the shaft may be coupled to a manual or powered rotational drive mechanism that may be controlled at the handle 118.

The blade may be positioned at any appropriate radial depth within the interior of the opening 302. In certain embodiments, the blade 304 may also be positioned directly over the outer lateral surface 106 of the rotatable member 102. Further, the blade 304 may be designed to have a radius of curvature substantially equal to that of the lateral surface 106 of the rotatable member 102, and in particular an interior surface of the rotatable member 102, to serve as a closure surface for the opening 302 during its idle conditions. In such cases, when being idle, the blade 304 may be extended distally along the direction indicated by the arrow 308, and slidably rotated in the direction of the arrow 306, to cover the opening 302. This may be advantageous while handling and steering the medical device 100 towards the target site through a body lumen, to prevent any internal injuries that may be caused by the sharp portions or edges of the blade 304 and/or the portions of the rotatable member 102 forming the opening 302.

It is also contemplated that the opening 302 may be in fluid communication with the vacuum source 130 by way of the conduit 142 and the one or more lumens 138. Suction force at and/or in the opening 302 may help draw a tissue layer onto the rotatable member 102 and/or into the opening 302. The rotatable member 102 may then be rotated to lift the tissue layer in the manner shown in FIGS. 2A-2D, using the actuation member 134, handle 118, and/or an associated actuation mechanism (not shown).

Figure 4:
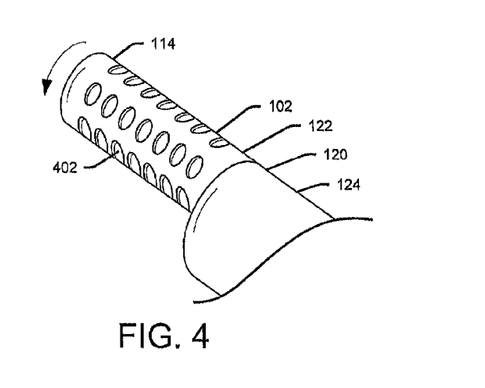
FIG. 4 is a partial perspective view of another exemplary medical device, in accordance with an embodiment of the present disclosure.

In some embodiments, a tissue engaging operation may be carried out using only suction on an outer surface of a rotatable member. One embodiment is shown in FIG. 4, where multiple vacuum openings 402, similar to the openings 108, may be provided on the outer surface 106 of the rotatable member 102 to act as a gripping element. The openings 402 may communicate with one or more lumens (not shown), disposed within the rotatable member 102, which in turn may communicate with the lumen 138 within the elongate member 124, and the vacuum source 130, similar to the arrangement shown in FIGS. 1A and 1B. Sufficient suction pressure maintained within the rotatable member 102, and at the openings 402, may lift up a layer of tissue onto the outer surface 106, and keep the tissue layer substantially fixed against the outer surface 106 during rotation of the rotatable member 102.

According to one embodiment, due to the suction forces at the openings 402 and the rotation of the rotatable member 102, a tissue layer may be wrapped around at least a portion of the rotatable member 102, in the manner shown in FIGS. 2A-2D. A portion of the engaged tissue layer may be cut using, for example, the cutting extender 210 and the cutting tool 206.

According to another embodiment, an area of tissue adjacent a portion of tissue targeted for cutting, resection, and/or dissection, may be engaged by the rotatable member 102. Suction forces at the openings 402 may lift and hold the area of tissue against the surface of the rotatable member 102. Rotation of the rotatable member 102 may pull the area of tissue, forming the area of tissue into a stepper wall, like a stepper wall 510 shown in FIG. 5B. Forming the stepper wall 510 may lift the targeted portion of tissue, similar to that which is shown in FIG. 5B, where a targeted portion of tissue is identified with reference number 506. With the stepper wall 510 formed, and the targeted tissue 506 positioned, a device, like an electro-cautery snare (not shown) or similar device, may be looped around the targeted portion of tissue 506 to cut, resect, and/or dissect the targeted portion of tissue 506. During such an operation, at least a portion of the snare may engage the stepper wall 510, with the stepper wall 510 facilitating gripping of the targeted portion of tissue 506 with the snare so the snare does not slip off. The electro-cautery snare may extend away from and retract toward the distal end 120 of the elongate member 124. At least a portion of the snare may extend from the proximal end 132 of the elongate member 124, and pass through a lumen in the elongate member 124, similar to the lumen 138. The snare may be controlled using the handle 118.

Additionally or alternatively, it is contemplated that cutting, resecting, and/or dissecting a tissue layer may be carried out with the rotatable member 102 by suction alone, without involving the need for a blade, hook, or any other cutting tools. Such a system may however be feasibly applicable to tissues that are relatively thinner and sensitive, and which may peel off from a bottom tissue layer.

Figure 5A:
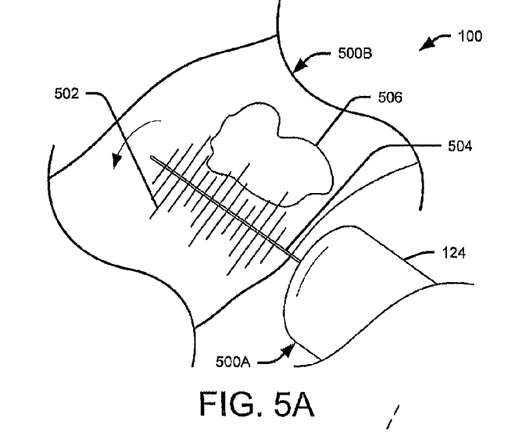
FIG. 5A is a partial perspective view of another exemplary medical device, in accordance with an embodiment of the present disclosure.
Figure 5B:
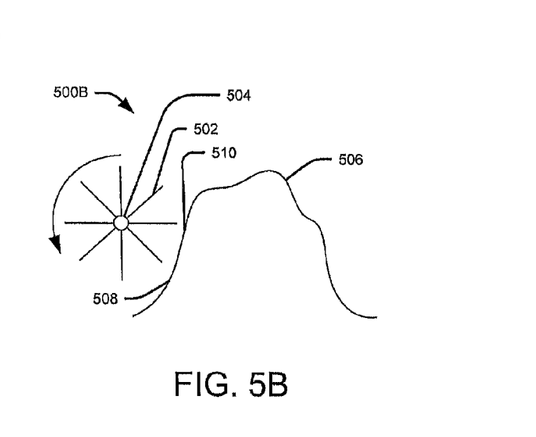
FIG. 5B is a partial end view of the medical device of FIG. 5A, in operation, in accordance with an embodiment of the present disclosure.

FIG. 5A depicts another embodiment 500A, wherein the rotatable member of the medical device 100 may have a different configuration for facilitating cutting, resection, and/or dissection of a layer of tissue. As shown, the rotatable member may include a rod 504. The rod 504 may have an array of protrusions 502, such as spikes, tangs, and/or hooks (shown schematically) provided over its outer surface, and/or along its longitudinal length, that may act as gripping elements. The rod 504 and protrusions 502 may be retractable into the distal end 120 of the elongate member 124, preventing them from injuring tissues while the medical device 100 is guided to a target site.

The protrusions 502 may enable lifting of a layer of tissue 500B by first gripping the tissue layer 500B. Gripping may be achieved by bringing the protrusions 502 into contact with the tissue layer 500B, and adhering the protrusions 502 to the tissue layer 500B by, for example, penetrating at least a portion of the tissue layer 500B with spikes, tangs, and/or hooks. After a grip has been established, the rod 504 may be rotated to lift the tissue layer 500B. The rod 504 may be rotated by, for example, the actuation member 134, the handle 118, and/or an associated actuation mechanism (not shown). Due to the engagement between the protrusions 502 and the tissue layer 500B, and further rotation of the rod 504, a portion of the tissue layer 500B may be wrapped around the rod 504 and protrusions 502, resulting in the tissue layer 500B being lifted and wrapped in a manner similar to that shown in FIGS. 2A-2D. A portion of the tissue layer 500B may be cut using, for example, the cutting extender 210 and the cutting tool 206, as shown in FIGS. 2A and 2D.

According to another embodiment, an area of tissue 508 adjacent a portion of tissue 506 targeted for cutting, resection, and/or dissection, may be engaged by the rod 504 and protrusions 502. The protrusions 502 may grip and hold the area of tissue 508, and rotation of the rod 504 may pull the area of tissue 508, forming the area of tissue 508 into the stepper wall 510. Forming the stepper wall 510 may lift the targeted portion of tissue 506. With the stepper wall 510 formed, and the targeted tissue 506 positioned, a device, like an electro-cautery snare (not shown) or similar device, may be looped around the targeted portion of tissue 506 to cut, resect, and/or dissect the targeted portion of tissue 506. During such an operation, at least a portion of the snare may engage the stepper wall 510, with the stepper wall 510 facilitating gripping of the targeted portion of tissue 506 with the snare so the snare does not slip off. The electro-cautery snare may extend away from and retract toward the distal end 120 of the elongate member 124. At least a portion of the snare may extend from the proximal end 132 of the elongate member 124, and pass through a lumen in the elongate member 124, similar to the lumen 138. The snare may be controlled using the handle 118.

Additionally or alternatively, it is contemplated that cutting, resecting, and/or dissecting a tissue layer may be carried out with the rod 504 and protrusions 502 by gripping and rotation alone, without involving the need for a blade, hook, or any other cutting tools. Such a system may however be feasibly applicable to tissues that are relatively thinner and sensitive, and which may peel off from a bottom tissue layer.

Figure 6:
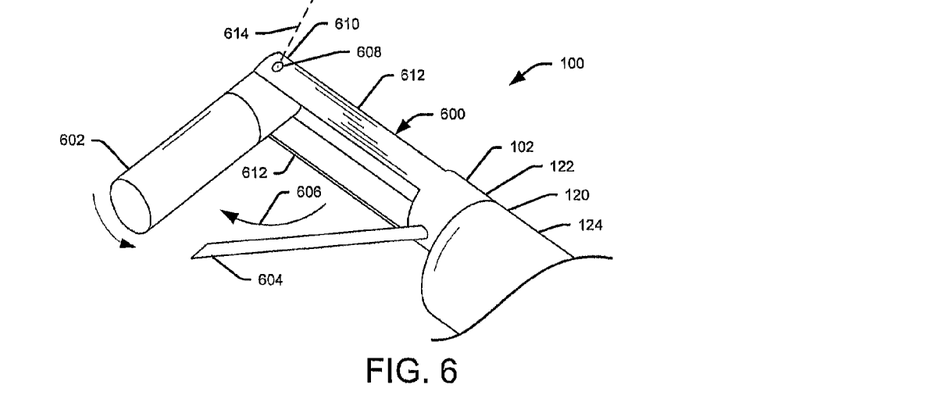
FIG. 6 is a partial perspective view of another exemplary medical device, in accordance with another embodiment of the present disclosure.

FIG. 6 depicts another embodiment of the present disclosure. The medical device 100 may include a clevis member 600, having arms 612, which may pivotally support a rotatable member 602. The rotatable member 602 may be similar in structure and operation to any of the rotatable members shown in FIGS. 1-5B. The rotatable member 602 may pivot or swivel around an axis of rotation 614. Specifically, the rotatable member 602 may pivot at a point 608 disposed at a distal end 610 of the clevis member 600. The point 608 may include a pin, axle, and/or any other suitable rotational connection. The axis 614 may be substantially perpendicular to a longitudinal axis of the rotatable member 602. Further, the clevis member 600 may be partially open faced, to receive the rotatable member 602 when the medical device 100 is being navigated to a target site through a body lumen or device lumen. The rotatable member 602 can be swiveled around the point 608 along and/or opposite the direction shown by the arrow 606, and may trace an arc of up to 360°, with the ability to stop at any position/orientation along the arc. Variations in the angular position of the rotatable member 602 may provide multiple angular operational positions, allowing the medical device 100, when equipped with the member 602, to cut, resect, and/or dissect tissue layers lying in otherwise hard-to-reach places. Swiveling of the rotatable member 602 may be controlled at the handle 118 using any suitable actuation member, like the actuation member 134, to connect the rotatable member 602 to the handle. The rotatable member 602 may engage a tissue layer, and/or lift a tissue layer, in the same manner as any of the rotatable members in FIGS. 1-5B.

Once the tissue layer has been lifted and positioned, a cutting tool 604, similar to the cutting extender 210 and cutting tool 206, may be actuated to cut, retract, and/or dissect the tissue layer. The cutting tool 604 may be extended, retracted, and/or pivoted about the clevis member 600, to be in position to cut the tissue layer. Additionally or alternatively, the rotatable member 602 may be used to grip and lift tissue to form the stepper wall 510 next to the lesion 506.

Figure 7A:
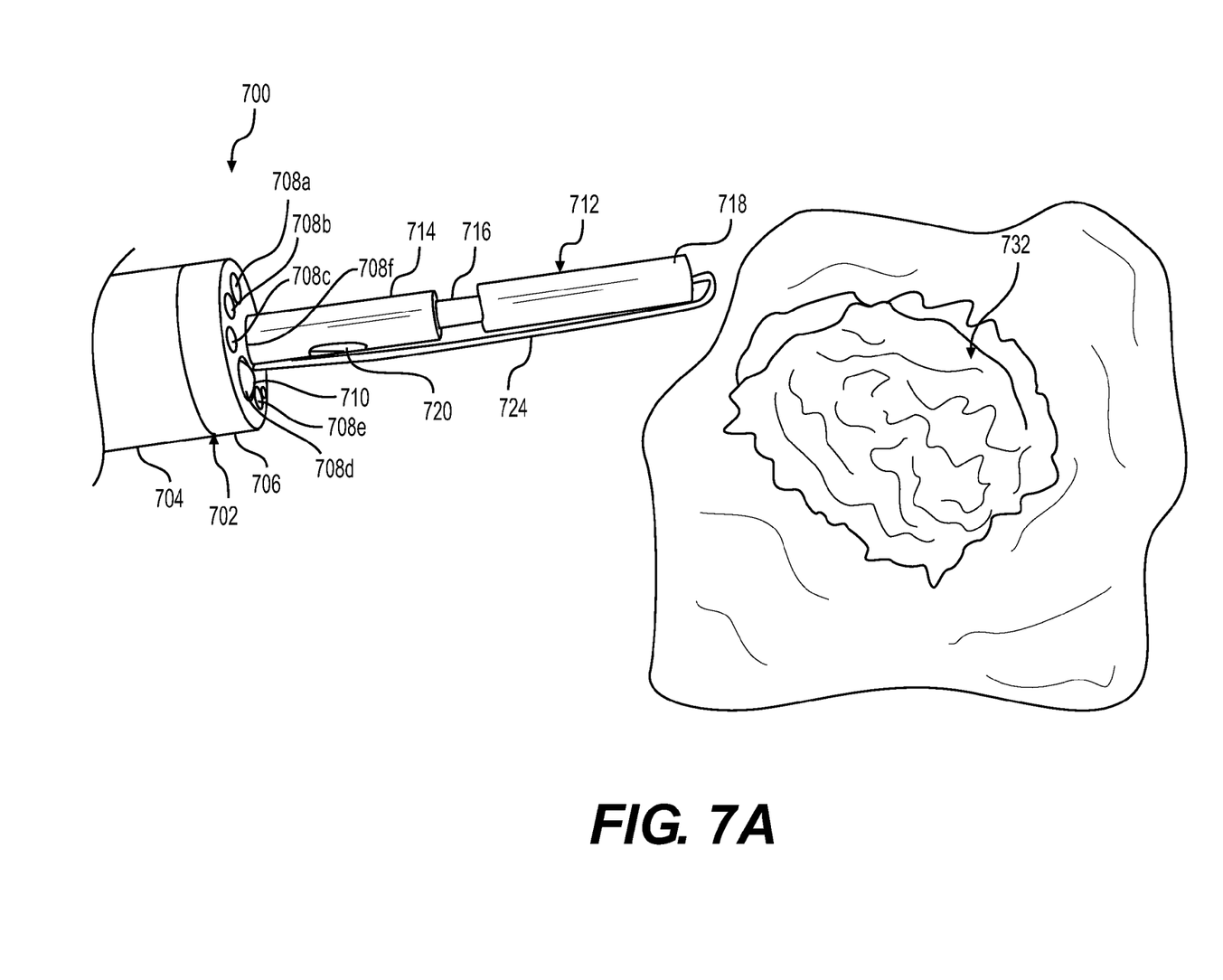
FIGS. 7A-7C are partial perspective views of another exemplary medical device, in accordance with another embodiment of the present disclosure.
Figure 7B:
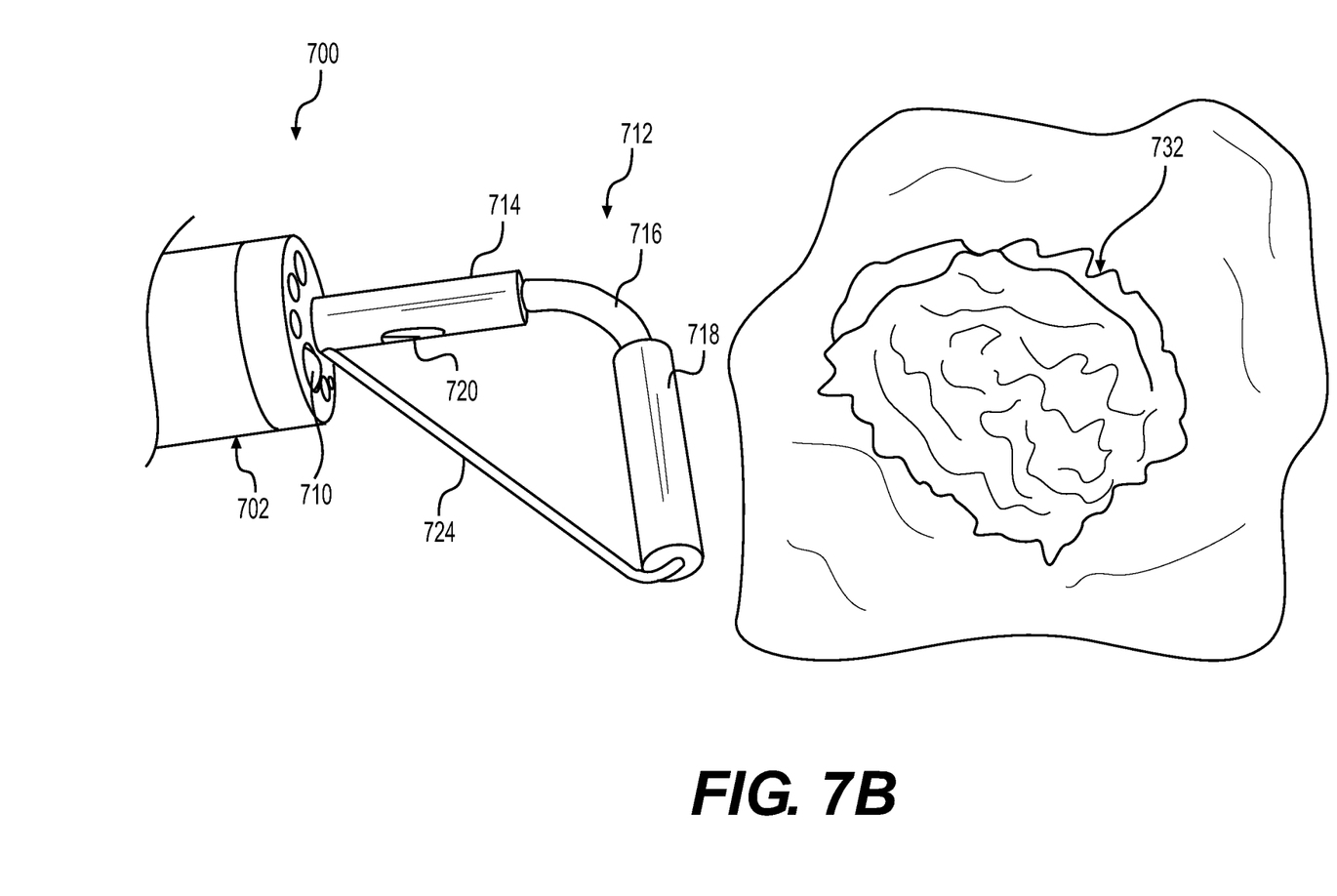
Figure 7C:
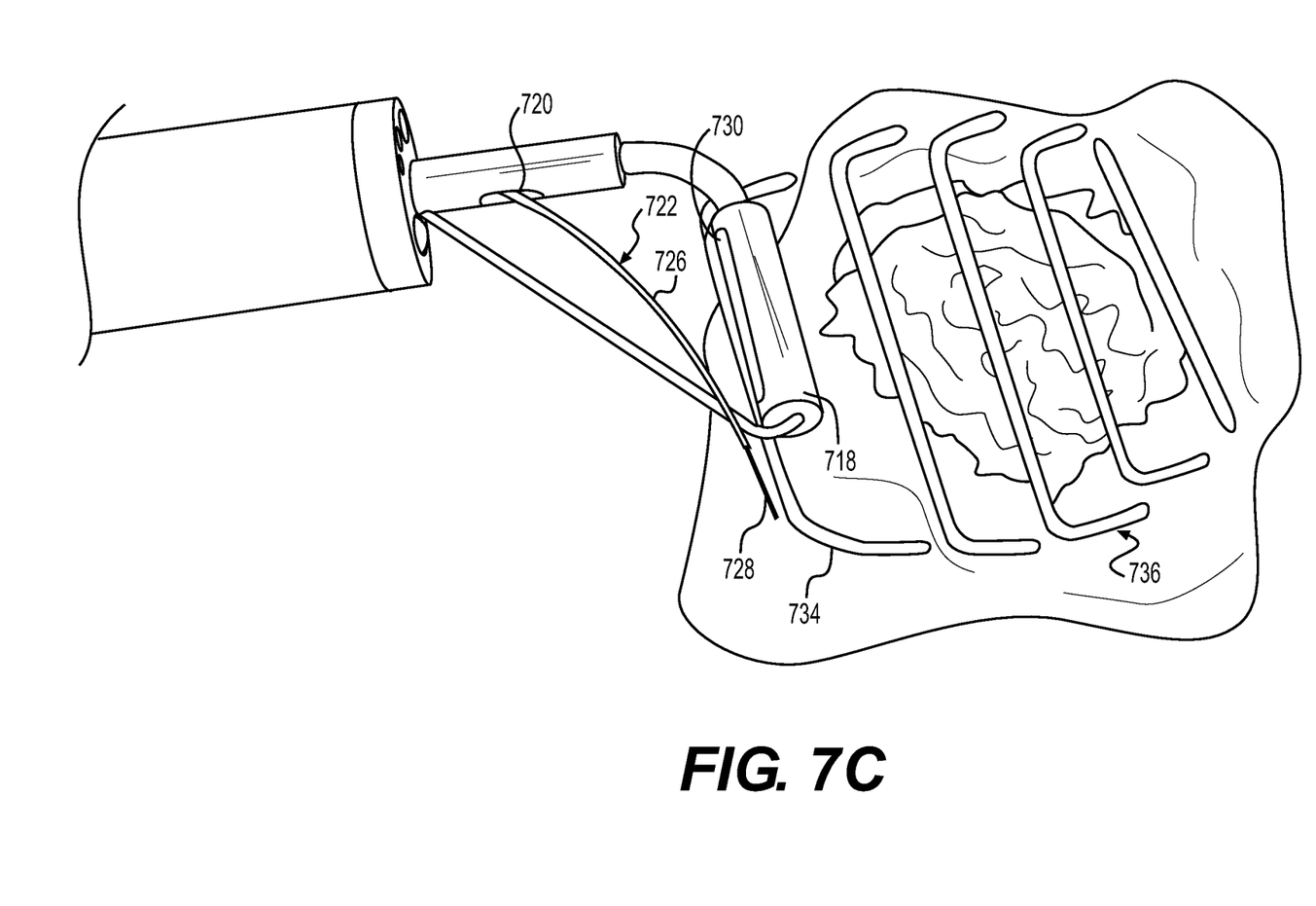

FIGS. 7A-7C depict another embodiment of the present disclosure. A medical device 700 may include an endoscope 702, or any other suitable sheath or catheter. The endoscope 702 may include a shaft 704 and a distal cap 706. The endoscope 702 may include one or more lumens (not shown) extending through the shaft 704 and cap 706, terminating at one or more distal openings 708*a*, 708*b*, 708*c*, 708*d*, 708*e*, and 708*f*. The lumen and distal opening 708*d* may be configured to house an imaging device 710, such as a camera or sensor.

The medical device 700 may also include an assembly 712 including a shaft 714, a bending member 716, and a rotatable member 718. The assembly 712 may be configured to be slidable in one of the lumens of the shaft 704 and cap 706, so a proximal portion of the assembly 712 can occupy a first position, extended out from the distal opening 708*f*. The proximal portion of the assembly 712 may also occupy a second position, in which the assembly 712 is covered by the shaft 704 and cap 706.

The shaft 714 may include one or more lumens (not shown), one of those lumens terminating at a side opening 720. A cutting device 722 (FIG. 7C) may be slidably disposed in the lumen, and may be extended out from the side opening 720 to cut tissue, and retracted within the side opening 720 when not in use. The cutting device 722 may include a wire or electrode with a proximal insulating sheath 726 and a distal exposed tip 728. The shaft 714 may also include a vacuum lumen (not shown) coupled to a vacuum source (not shown), to generate a vacuum force at the rotatable member 718. The shaft 714 may also include a rotational drive transmission mechanism (not shown), such as a torque transmitting shaft, for rotating the rotatable member 718.

The bending member 716 may be substantially resilient. The bending member 716 may be biased toward a straight configuration (FIG. 7A). Under force, the bending member 716 may be bent into a curved configuration (FIGS. 7B and 7C). When bent, the bending member 716 may swing the rotatable member 718 across an arc of between approximately 90° to 180°. The bending member 716 may be bent by pulling a cord or wire 724, coupled to the rotatable member 718, in a proximal direction. When the pulling force is removed, the bending member 716 may move back to its straight configuration. The wire 724 may run alongside the shaft 714 in the same lumen as the shaft 714. The bending member 716 may be made of a resilient material, one or more spring devices, and/or spring-biased articulation links.

The rotatable member 718 may include the features of any of the rotatable members in FIGS. 1A-6. For example, the rotatable member 718 may include a vacuum slot 730. A vacuum force within the rotatable member 718 may draw tissue into the slot 730, similar to the operation of the rotatable member 102.

In operation, the endoscope 702 may be navigated through one or more body lumens to a target area in a patient's body. The target area may include a region of tissue 732, such as a lesion, for removal. When the endoscope 702 is in position, the assembly 712 may be moved distally to expose the rotatable member 718, bending member 716, and a portion of the shaft 714, from a distal end of the endoscope 702. The assembly 712 may be extended toward the tissue 732, with positioning of the assembly 712 being assisted by the imaging device 710.

Once the assembly 712 is in a desired position at or near the tissue 732, the wire 724 may be pulled proximally to bend the bending member 716, and swing the rotatable member 718 about an arc. The rotatable member 718 may be swung about an axis substantially perpendicular to a longitudinal axis of the endoscope 702 and/or the shaft 714. This positions the rotatable member 718 in a desired position relative to the tissue 732.

The cutting device 722 may be extended out from the side opening 720. The edges of the side opening 720 may be inclined to direct the cutting device 722 in a lateral direction, as shown in FIG. 7C. The cutting device 722 may be used to make a cut 734 (by, for example, burning the tissue 732) adjacent and substantially parallel to the rotatable member 718. The tissue 732 may curl up at the cut 734. It is contemplated that the cut 734 may be C-shaped.

The curled up tissue 732, and/or any other part of the tissue adjacent the cut 734, may be drawn into the vacuum slot 730. The rotatable member 718 may be rotated to lift or peel the tissue 732. Additional cuts 736, similar to the cut 734, may be made at intervals to loosen up more of the tissue 732 as the rotatable member 718 continues to roll and peel back the tissue.

It will be apparent to those skilled in the art that various modifications and variations can be made in the disclosed systems and processes without departing from the scope of the disclosure. Other embodiments of the disclosure will be apparent to those skilled in the art from consideration of the specification and practice of the aspects disclosed herein. It is intended that the specification and examples be considered as exemplary only, with a true scope and spirit of the disclosure being indicated by the following claims.

What is claimed is:

1. A medical device, comprising:
an elongate member including a proximal end and a distal end;
a rotatable member at the distal end of the elongate member, wherein:
the rotatable member is rotatably coupled to the distal end of the elongate member,
the rotatable member includes a central longitudinal axis, and is configured to rotate about the central longitudinal axis,
the rotatable member includes a gripping element configured to engage a layer of tissue, and
the gripping element is configured to selectively couple at least a portion of the layer of tissue to a surface of the rotatable member, to restrict relative movement between the portion of the layer of tissue and the surface of the rotatable member, during rotation of the rotatable member;
a handle at the proximal end of the elongate member, wherein the handle includes an actuator operatively coupled to the rotatable member to control rotation of the rotatable member about the central longitudinal axis of the rotatable member; and
a rotatable blade within the rotatable member.

2. The medical device of claim 1, wherein the longitudinal axis of the rotatable member is substantially parallel to a longitudinal axis of the elongate member.

3. The medical device of claim 1, wherein the rotatable member is substantially cylindrical.

4. The medical device of claim 1, wherein an axis of rotation of the rotatable blade is one of coaxial with and parallel to the axis of rotation of the rotatable member.

5. The medical device of claim 1, wherein the rotatable member includes at least one lateral opening.

6. The medical device of claim 5, wherein the at least one lateral opening includes a slot defined by the rotatable member.

7. The medical device of claim 6, wherein a surface of the slot defines at least one suction opening.

8. The medical device of claim 7, wherein the at least one suction opening is configured to be fluidly coupled to a vacuum source by a vacuum lumen extending through the elongate member.

9. A medical device, comprising:
an elongate member including a proximal end and a distal end;
a rotatable member at the distal end of the elongate member, wherein:
the rotatable member is rotatably coupled to the distal end of the elongate member,
the rotatable member includes a longitudinal axis, and is configured to rotate about the longitudinal axis,
the rotatable member includes a gripping element configured to engage a layer of tissue, and
the gripping element is configured to selectively couple at least a portion of the layer of tissue to a surface of the rotatable member, to restrict relative movement between the portion of the layer of tissue and the surface of the rotatable member, during rotation of the rotatable member; and
a rotatable blade within the rotatable member.

10. The medical device of claim 9, wherein an axis of rotation of the rotatable blade is one of coaxial with and parallel to the axis of rotation of the rotatable member.

* * * * *